United States Patent
Huang et al.

(10) Patent No.: US 7,350,396 B2
(45) Date of Patent: Apr. 1, 2008

(54) PULSE-TYPE GAS CONCENTRATION MEASUREMENT SYSTEM AND METHOD THEREOF

(75) Inventors: Yih-Shiaw Huang, Hsinchu (TW); Miao-Ju Chueh, Hsinchu (TW); I-Cherng Chen, Hsinchu (TW); Tung-Sheng Shih, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 818 days.

(21) Appl. No.: 10/743,742

(22) Filed: Dec. 24, 2003

(65) Prior Publication Data
US 2005/0045494 A1    Mar. 3, 2005

(30) Foreign Application Priority Data
Aug. 28, 2003    (TW)    .............................. 92123697 A

(51) Int. Cl.
*G01N 27/26*    (2006.01)
(52) U.S. Cl. ...................... 73/23.2; 73/31.06
(58) Field of Classification Search ................ 73/23.2, 73/31.06, 25.01, 25.05; 702/24
See application file for complete search history.

(56) References Cited

U.S. PATENT DOCUMENTS 6,739,180 B2 *    5/2004    Huang et al. .............. 73/31.06

* cited by examiner

*Primary Examiner*—Daniel S. Larkin
(74) *Attorney, Agent, or Firm*—Birch, Stewart, Kolasch & Birch, LLP

(57) ABSTRACT

A pulse-type gas concentration measurement system and a method of pulse-type gas concentration measurement in a specific environment. When the sensor is located at a specific position, a variable pulse-modulated voltage is sent to the sensor, so that the sensor outputs a first signal to the processing device. The processing device compares the first signal to the chemical matter characteristics signals to determine the composition and concentration of respective constituents in the gas, and determines a detection voltage according to the first signal. Then, a square-wave pulse with the detection voltage is sent intermittently to the sensor, so that the sensor outputs a second signal to the processing device. The processing device compares the second signal to the chemical matter characteristics signal to determine the concentration variation of each respective constituent of the gas.

17 Claims, 8 Drawing Sheets

PULSE-TYPE GAS CONCENTRATION MEASUREMENT SYSTEM AND METHOD THEREOF

This Nonprovisional application claims priority under 35 U.S.C. § 119(a) on Patent Application No(s). 92123697 filed in TAIWAN on Aug. 28, 2003, the entire contents of which are hereby incorporated by reference.

BACKGROUND OF THE INVENTION

1. Field of the Invention

The present invention relates to a pulse-type gas concentration measurement system and a method for pulse-type concentration measurement for volatile chemical matter in a specific environment.

2. Brief Discussion of the Related Art

Conventionally, a gas concentration sensor is used for obtaining the concentration of a specific gas. An example of a conventional gas concentration sensor 500 is described in detail with reference to FIG. 1A and FIG. 1B.

The conventional gas concentration sensor 500, as shown in FIG. 1A, has a body 510, voltage input elements 520, and output elements 530. The body 510, as shown in FIG. 1B, has a substrate 512, electrodes 514, a sensing element 516, and a heater 518. Generally, the sensing element 516 is a metallic oxide membrane, such as a tin dioxide ($SnO_2$) membrane, which reacts to a specific gas in the vicinity of the gas concentration sensor 500. When the conventional gas concentration sensor 500 is applied in a specific environment to measure gas concentration, a fixed voltage is input to the sensor 500 through the voltage input element 520 to activate the heater 518, to heat the membrane of the sensing element 516 to a predetermined temperature, such as 400° C. Thus, the membrane of the sensing element 516 reacts to the specific gas to be measured in the specific environment, and the resistance of the sensing element 516 changes due to the reaction. An outgoing voltage, determined by the resistance of the sensing element 516, is then obtained by the output element 530 as an outgoing signal.

It is obvious that the concentration of the specific gas in the specific environment affects the reaction, and the relation between the concentration of the specific gas and the resistance of the sensing element 516 can be established by experiment as a reference for the gas concentration sensor 500.

FIG. 2A is a chart showing an example of gas concentration measurement using the conventional gas concentration sensor 500, in which the curves L1 and L2 respectively refer to different concentrations of the specific gas. When the voltage is input to the sensor 500 through the voltage input element 520 to activate the heater 518, the membrane of the sensing element 516 is heated to a predetermined temperature, such as 400° C. In both cases, the resistance of the sensing element 516 changes due to the reaction, inducing an outgoing voltage (shown as point A) with concentration L1 and point B with concentration L2. It should be noted that the predetermined temperature of the conventional gas concentration sensor 500 is generally set to a preferred temperature, in which the outgoing voltage is significant, so that responses of the gas concentration sensor 500 are obvious. Fox example, the preferred temperature shown in FIG. 2A is approximately 400° C.

The conventional gas concentration sensor 500 has a membrane-type structure, which has a relatively low cost. Further, the conventional gas concentration sensor 500 reacts to the gas to be measured rapidly and can be used effectively for a long period of time. As a result, the gas concentration sensor is widely used. For example, U.S. Pat. No. 6,336,354 discloses a gas concentration measuring apparatus, in which a gas concentration sensor is applied, using a heat control circuit to supply power to the heater of the sensor cyclically using a pulse-modulated (PM) signal. In this case, the apparatus corrects errors contained in the gas concentration signal, regulating the signal, and the outgoing signal of the gas concentration sensor is significant.

The conventional gas concentration sensor 500, however, is used mainly to measure the concentration of a specific gas. It is obvious that the conventional gas concentration sensor 500 can be used in a specific environment when the specific gas exists in the specific environment. The membrane of gas concentration sensor 500, however, may react to a plurality of gases. Thus, when more than one of the gases exists in the specific environment, the conventional gas concentration sensor 500 cannot distinguish between each gas, so that the outgoing signal of the gas concentration sensor 500 does not correspond exactly to a specific gas, and gas concentrations are not accurately obtained. Additionally, when the composition of the gas in the specific environment is unidentified, the conventional gas concentration sensor 500 cannot determine the composition of the gas.

In a gas concentration measurement, a fixed voltage is input to a sensor to activate a heater, thus heating the membrane of the sensing element to react with the specific gas to be measured in the specific environment, and the resistance of the sensing element changes due to the reaction. An outgoing signal is thus obtained. The fixed voltage is generally set to heat the membrane of the sensing element to a preferred temperature. However, if the voltage input to the sensor is changed, the outgoing signal also changes.

FIG. 2B is a chart showing outgoing signals corresponding to a plurality of gases measured by a sensor. The gases include hydrogen (H2), carbon monoxide (CO), ethanol (C2H5OH), methane (CH4) and butane (C4H10), and the concentration of each gas is kept at 0.1% to obtain the outgoing signals. The sensor applied is a widely-used conventional gas concentration sensor as described above. It should be noted that the curves of FIG. 2B show that the outgoing signals of the gases change corresponding to the membrane temperature (that is, the voltage input to the sensor), and each outgoing signal can be recognized as a distinctive pattern. Thus, the outgoing signal of the gas can be used as a chemical matter characteristics signal of the gas for use in gas identification.

The gas identification method in FIG. 2B can be further described in comparison to the gas concentration measurement, as shown in FIG. 2A. In FIG. 2A, the outgoing signal of the gas concentration sensor 500 is a point, related to a fixed membrane temperature (due to the fixed voltage input to the sensor 500), such as the preferred temperature. However, in FIG. 2B, the outgoing signal of the sensor is a curve related to a specific range of membrane temperature, applied as determined by the chemical matter characteristics signal of the gas in association the inventor has proposed an intelligent gas identification system and method thereof, which is disclosed in Taiwan Patent No. 531139. In the intelligent gas identification system and method thereof, a pulse-modulated (PM) signal is used as the input voltage to the conventional gas concentration sensor so that the outgoing signals corresponding to various gases differ. Thus, a chemical matter characteristics database can be established by experiment, and the chemical matter characteristics can be used as a reference to determine the composition and/or concentration of the gases.

Specifically, Taiwan Patent No. 531139 utilizes the gas identification method shown in FIG. 2B, which can be further described with respect to FIG. 3A and FIG. 3B, also of this disclosure.

FIG. 3A shows the intelligent gas identification system disclosed in Taiwan Patent No. 531139. The intelligent gas identification system is applied to perform gas identification (or volatile chemical matter identification) in a specific environment, which has a sensor 10, a pulse power supply module 20, and a processing device 30.

The sensor 10, which can be a conventional gas concentration sensor 500 as shown in FIG. 1A, has at least a voltage input element, at least an output element, and a sensing element (that is, the body 510). The sensing element can be a metallic oxide membrane, such as a tin dioxide membrane ($SnO_2$), which reacts to the specific gas in the vicinity of the sensor 10.

The pulse power supply module 20 is connected to the voltage input element of the sensor 10 to send a variable pulse-modulated voltage to the sensor 10, so that the sensor 10 sends out an outgoing signal through the output element.

The processing device 30 can be a computer with a pattern recognition module and a database for storing a plurality of chemical matter characteristics signals. The pattern recognition module, for example, can be graphic recognition software. Further, the processing device 30 receives an outgoing signal from the output element of the sensor 10.

When the intelligent gas identification system is used to perform gas identification, the sensor 10 is disposed in the specific environment. The pulse power supply module 20 sends a variable pulse-modulated voltage to the sensor 10 through the voltage input element, so that the membrane of the sensing element is reiteratively heated, and in each heating process, the membrane temperature varies due to the variable pulse-modulated voltage. Thus, the membrane reacts to the gas in the specific environment with different temperature, and the sensor 10 sends out an outgoing signal, such as a variable pulse-modulated signal, to the processing device 30. Then, the processing device 30 compares the outgoing signal with the chemical matter characteristics signals to determine an identification result for the gas, such as composition of the gas, and/or concentration of the respective constituents of the gas.

The method of gas identification disclosed in Taiwan Patent No. 531139 can be described with reference to the flowchart of FIG. 3B. According to FIG. 3B, it is assumed that a gas G to be identified exists in a specific environment, and two given chemicals X and Y are provided for comparison to the gas G. That is, the gas identification is performed to determine if the gas G matches X or Y exactly.

When gas identification is performed, a sensor 10 as mentioned is provided (step S10) and disposed in the given chemicals X and Y (step S20). Then, a variable pulse-modulated voltage is provided to the sensor 10 respectively, so that the sensor 10 outputs the chemical matter characteristics signals SX, SY for the given chemicals X and Y (step S30). The chemical matter characteristics signals SX and SY can then be stored in a database (step S40) for further identification of the gas G.

The sensor is then disposed in the specific environment with the gas G (step S50). The sensor is provided with a variable pulse-modulated voltage, so that the sensor outputs an outgoing signal SG corresponding to the gas G in the specific environment (step S60). Thus, the processing device 30 receives the outgoing signal SG and compares the outgoing signal SG to the chemical matter characteristics signals SX and SY to determine an identification result for the gas G (step S70).

Preferably, the intelligent gas identification system and method thereof is utilized in a specific environment, in which the gas G to be identified is unknown. For example, the intelligent gas identification system is suited to a semi-open environment, in which composition of the gas G is variable.

In some cases, however, the specific environment is an airtight environment that has a fixed composition of the gas G, or an environment in which the composition of the gas G is already known. For example, in a laboratory or a semiconductor fab, it is well known that a chemical reaction or a manufacturing process may produce certain types of gases. Thus, composition of the gas in the laboratory or the semiconductor fab is fixed in a group of these types of gases. It should be noted that the above-mentioned process of receiving the outgoing signal SG and comparing the outgoing signal to the chemical matter characteristics signals SX and SY can be performed only once to determine or confirm the composition of the gas G. Accordingly, the intelligent gas identification system and method is complicated and can be further simplified.

Further, the sensitivity of the sensor 10 can be strongly influenced by environmental factors, such as temperature or air flow rate, in which temperature is the most critical factor. Accordingly, a low-temperature environment has a destabilizing effect on the relationship between the outgoing voltage and the input voltage, resulting in inaccurate gas identification.

SUMMARY OF THE INVENTION

Accordingly, an object of the present invention is to provide a pulse-type gas concentration measurement system and method thereof, which is modified according to the above-mentioned intelligent gas identification system and method thereof. When the pulse-type gas concentration measurement system and method is utilized to identify the specific environment in which the gas composition is fixed or known, the detection process is simplified, and power consumption of the sensor is reduced.

Another object of the present invention is to provide a pulse-type gas concentration measurement system and method thereof, in which the effect of environmental factors, such as temperature, can be reduced by using voltage input and output control of the sensor.

To achieve foregoing and other objects, the present invention discloses a pulse-type gas concentration measurement system. The pulse-type gas concentration measurement system has a sensor, a pulse power supply module, and a processing device. The sensor has a voltage input element, an output element and a sensing element and is disposed in a specific environment to perform gas concentration measurement. Gas in the specific environment may have at least two compositions. The pulse power supply module is connected to the voltage input element. The processing device stores a plurality of chemical matter characteristics signals and receives the outgoing signal from the output element of the sensor. When the pulse power supply module sends a variable pulse-modulated voltage to the sensor through the voltage input element, the sensor outputs a first signal to the processing device through the output element, and the processing device determines a detection voltage according to the first signal and compares the first signal with the chemical matter characteristics signals to determine composition of the gas and concentration of respective constituents of the gas. On the other hand, when the pulse power supply module sends a square-wave pulse with the detection voltage to the sensor through the voltage input element, the sensor outputs a second signal to the processing device through the output element, and the processing device compares the second signal to the chemical matter characteristics signal to determine the concentration of respective constituents of the gas.

Further, the present invention discloses a method of gas concentration measurement. First, a sensor is provided in a specific environment. The sensor is provided with a variable pulse, which can be a pulse-modulated (PM) voltage, so that the sensor outputs a first signal corresponding to a gas in the specific environment. The first signal is compared with a plurality of chemical matter characteristics signals to determine a first identification result for the gas, which can be the composition of the gas. A detection voltage is determined according to the first signal. Then, a square-wave pulse with the detection voltage is sent to the sensor, so that the sensor outputs a second signal corresponding to the gas. The second signal is compared with a plurality of chemical matter characteristics signals to determine a second identification result for the gas as a concentration result.

In the method of gas concentration measurement, the chemical matter characteristics signals can be obtained by exposing the sensor in a plurality of predetermined chemical matter and sending a variable pulse-modulated voltage to the sensor respectively, so that the sensor outputs each of the chemical matter characteristics signals corresponding to each of the predetermined chemicals. Chemical matter characteristics signals can then be stored in a database.

Further, the detection voltage according to the first signal can be determined by determining an ideal voltage related to a maximum voltage of the first signal from the variable pulse. Thus, the detection voltage is determined as a voltage larger than the ideal voltage.

In the present invention, the sensing element can be a metallic oxide membrane, such as tin dioxide (SnO2) membrane. Further, the second identification result can be the concentration of the respective constituents of the gas. With the present invention, a single sensor can be used to identify concentrations of at least two compositions of gases at the same time.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the subsequent detailed description and the accompanying drawings, which are given by way of illustration only, and thus are not limitative of the present invention, and wherein.

DETAILED DESCRIPTION OF THE INVENTION

In gas concentration measurement a fixed voltage is input to the sensor to obtain an outgoing signal related to the concentration of the gas. The fixed voltage is generally set to heat the membrane of the sensor to a preferred temperature. Further, in the above-mentioned intelligent gas identification system and method thereof, a pulse-modulated (PM) signal is used as the input voltage to the conventional gas concentration sensor so that the outgoing signals corresponding to various gases differ. Thus, a chemical matter characteristics database can be established by experiment, and the chemical matter characteristics can be used as a reference for determining the composition and/or concentration of the gases. The method to be introduced in the present invention is a further implementation of the method disclosed in the above-mentioned intelligent gas identification system and method thereof.

Figure 5:
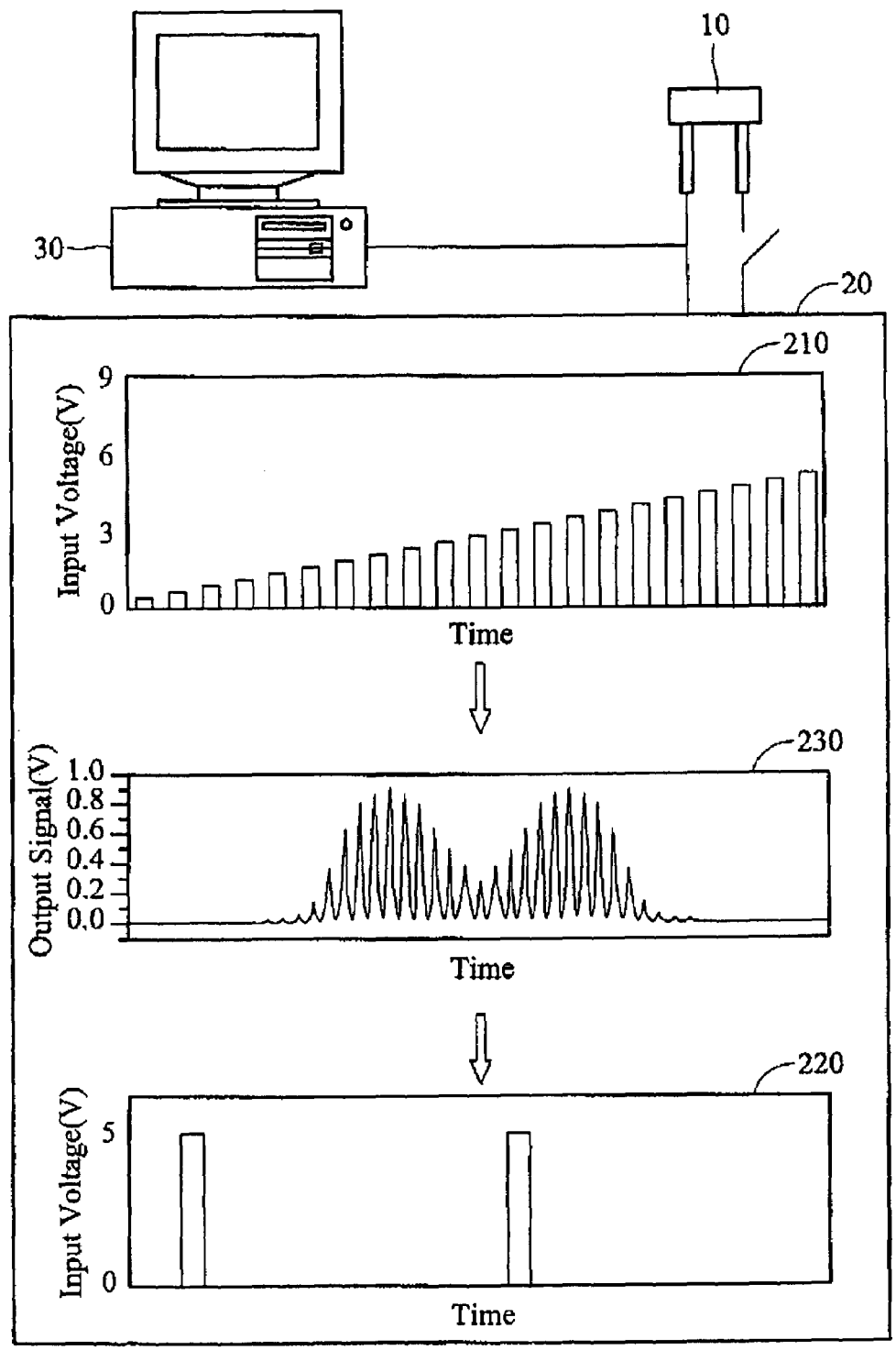
FIG. 5 is a schematic view showing an embodiment of the pulse-type gas concentration measurement system of the present invention.

An embodiment of the pulse-type gas concentration measurement system of the present invention is hereinafter described with reference to FIG. 5. The pulse-type gas concentration measurement system of the present invention is applied to perform gas concentration measurement (or volatile chemical matter concentration measurement) in a specific environment. The pulse-type gas concentration measurement system has a sensor 10, a pulse power supply module 20, and a processing device 30.

Figure 1A:
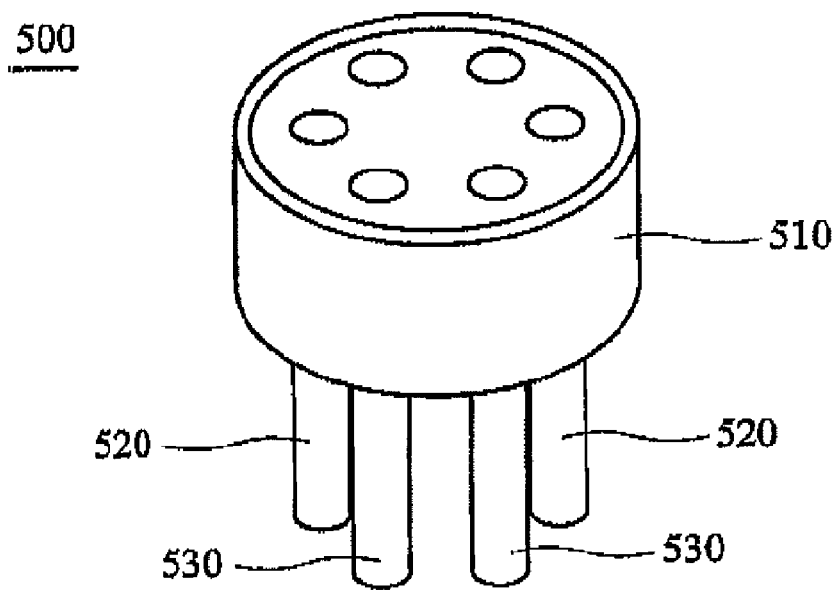
FIG. 1A is a schematic view of a conventional gas concentration sensor.
Figure 1B:
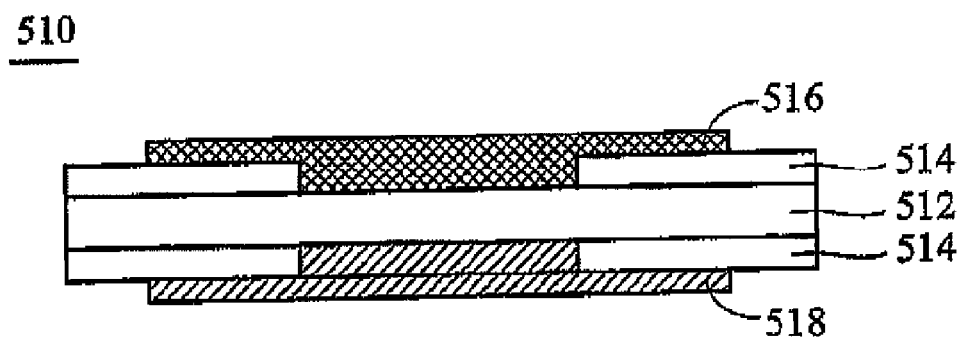
FIG. 1B is a schematic view of the body of the conventional gas concentration sensor.

The sensor 10, which can be a conventional gas concentration sensor 500 as shown in FIG. 1A, has at least a voltage input element, at least an output element, and a sensing element (that is, the body 510). The sensing element can be a metallic oxide membrane, is such as a tin dioxide membrane ($SnO_2$), which reacts to the specific gas in the vicinity of the sensor 10.

The pulse power supply module 20 is connected to the voltage input element of the sensor 10 to send an input voltage, which can be variable pulse-modulated voltage or a square-wave pulse, to the sensor 10, so that the sensor 10 sends out an outgoing signal through the output element.

The processing device 30 can be a computer with a pattern recognition module and a database for storing a plurality of chemical matter characteristics signals. The pattern recognition module, for example, can be graphic recognition software. Further, the processing device 30 receives an outgoing signal from the output element of the sensor 10.

Comparison of the pulse-type gas concentration measurement system of the present invention and the intelligent gas identification system mentioned in the related art can be described with reference to FIGS. 4A to 4C and FIG. 5.

Figure 2A:
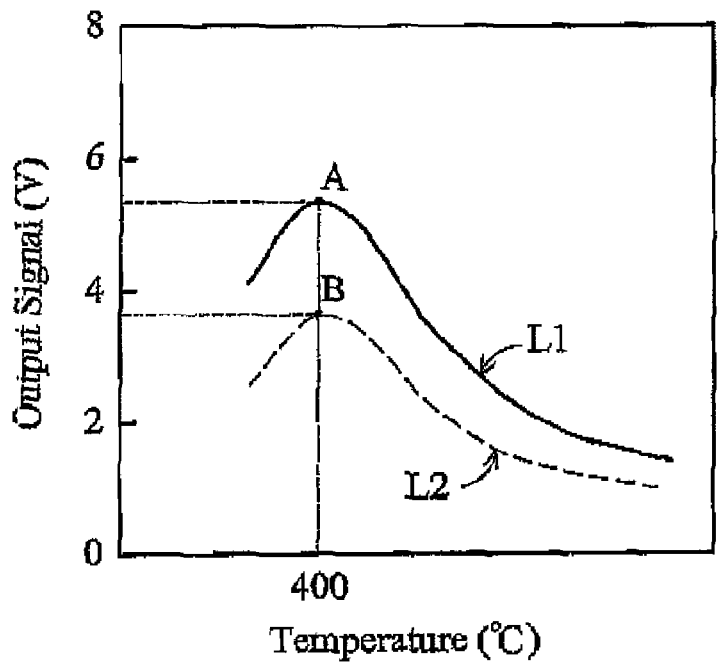
FIG. 2A is a chart showing the outgoing signals corresponding to a specific gas with various concentrations as output by the conventional gas concentration sensor.
Figure 2B:
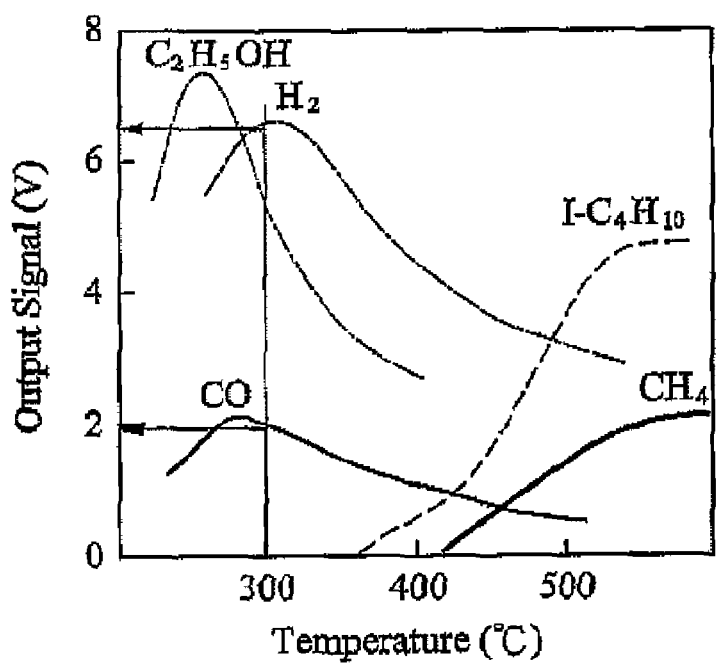
FIG. 2B is a chart showing the outgoing signals corresponding to various gases as output by the conventional gas concentration sensor.
Figure 4A:
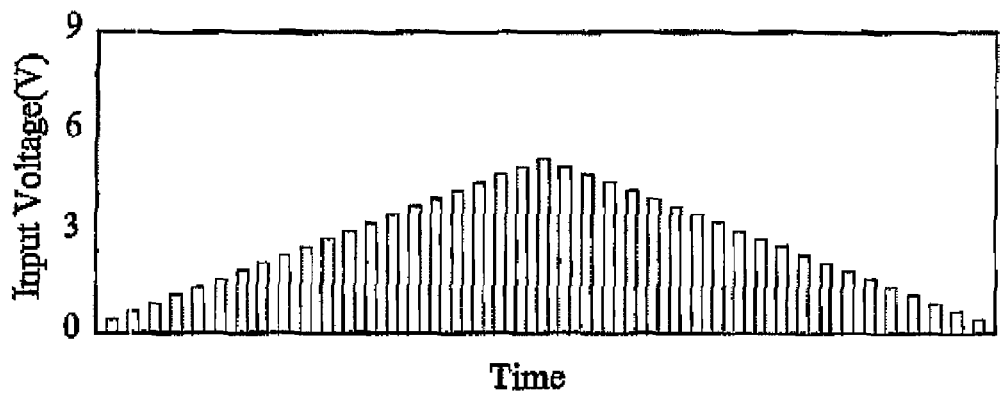
FIG. 4A is a schematic chart showing the variable pulse-modulated voltage in the embodiment of the present invention.
Figure 4B:
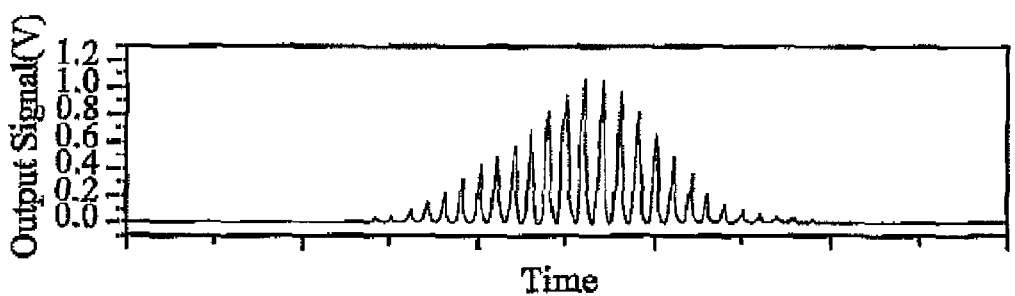
FIG. 4B is a chart showing the chemical matter characteristics signal corresponding to methane with a concentration of 2000 ppm.
Figure 4C:
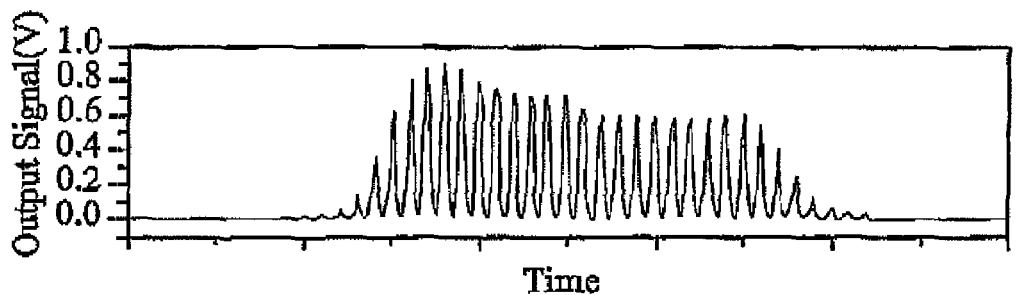
FIG. 4C is a chart showing the chemical matter characteristics signal corresponding to hydrogen with a concentration of 2000 ppm.

When the pulse-type gas concentration measurement system of the embodiment is used to perform gas concentration measurement, the sensor 10 is disposed in the specific environment. The pulse power supply module 20 sends a variable pulse, which can be a variable pulse-modulated voltage 210 within a range of 0V to 6V as shown in FIG. 4A, to the sensor 10 through the voltage input element, so that the membrane of the sensing element is reiteratively heated, and in each heating process, the membrane temperature varies due to the variable pulse-modulated voltage. Thus, the membrane reacts to the gas in the specific environment with different temperature, and the sensor 10 outputs a first signal, such as a variable pulse-modulated signal 230, as the outgoing signal to the processing device 30. The processing device 30 then compares the first signal 230 with the chemical matter characteristics signals. The chemical matter characteristics signals are related to a plurality of signals as shown in FIG. 2B, e.g. a chemical matter characteristics signal corresponding to methane with a concentration of 2000 ppm as shown in FIG. 4B, and the chemical matter characteristics signal corresponding to hydrogen with a concentration of 2000 ppm as shown in FIG. 4C, to determine a first identification result for the gas, such as composition of the gas, and/or concentration of the respective constituents of the gas. Since gas in the specific environment may have at least two compositions, the compositions can be recognized from the first identification result in comparison to the chemical matter characteristics signals.

Meanwhile, the processing device 30 determines a detection voltage according to the first signal, which is the critical difference between the pulse-type gas concentration measurement system of the present invention and the intelligent gas identification system. Specifically, the processing device 30 obtains a maximum voltage of the first signal, and determines an ideal voltage from the variable pulse-modulated voltage, which is related to the maximum voltage of the first signal. Thus, the detection voltage can be obtained as a voltage larger than the ideal voltage.

For example, when the gas in the specific environment is pure methane, the ideal voltage can be obtained as 5.8V according to FIG. 4B. Thus, the first detection voltage can be determined as 6V, which is larger than the ideal voltage of 5.8V. Conversely, when the gas in the specific environment is pure hydrogen, the ideal voltage can be obtained as 4.8V according to FIG. 4C. Thus, the second detection voltage can be determined as 5V, which is larger than the ideal voltage of 4.8V. It should be noted that two maximum voltages can be obtained in the first signal when the gas in the specific environment is a mixture of methane and hydrogen. In this case, two ideal voltages of 5.8V and 4.8V can be obtained, and two detection voltages of 6V and 5V can be determined.

Figure 6A:
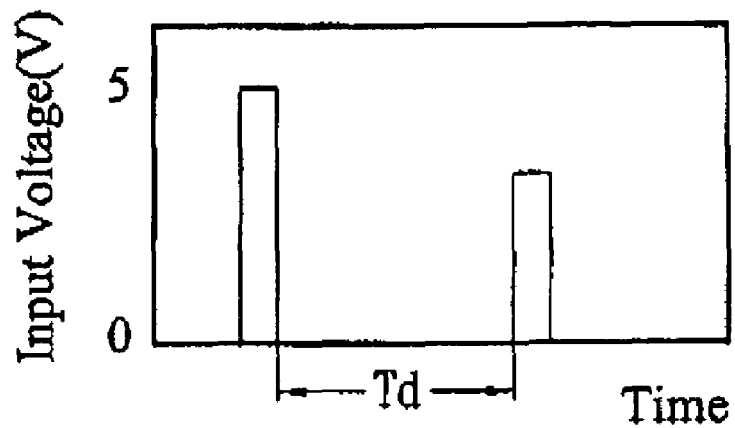
FIG. 6A is a chart showing an embodiment of square-wave pulse 220.
Figure 6B:
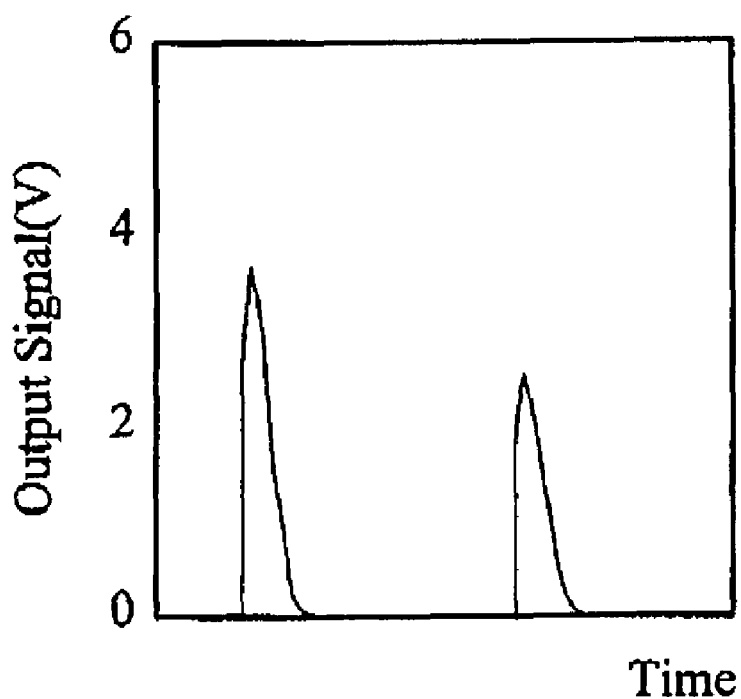
FIG. 6B is a chart showing a pulse voltage (the second signal) corresponding to FIG. 6A.

The pulse power supply module 20 then sends a square-wave pulse 220 with the two detection voltages, which is shown in FIG. 6A, to the sensor 10 through the voltage input element. Thus, the sensor 10 outputs a second signal, such as a pulse in FIG. 6B, to the processing device 30 through the output element, and the processing device 30 compares the second signal to the chemical matter characteristics signal to determine the second identification result of the gas as the gas concentration result, such as concentration of respective constituents of the gas.

It should be noted that the detection voltage can be determined as a voltage larger than the ideal voltage. The reason for this determination is hereafter described with reference to FIG. 2.

The ideal voltage is related to the maximum voltage of the first signal. Ideally, when the ideal voltage is utilized as the input voltage of the sensor 10, the outgoing signal of the sensor 10 reaches a maximum value, such as point A or point B in FIG. 2. In practical use, however, the membrane temperature of the sensor 10 may be lower than the ideal temperature related to the ideal voltage since the sensor 10 will be affected by environmental factors, such as temperature. As a result, when the detection voltage is determined as a voltage larger than the ideal voltage, the membrane temperature of the sensor 10 may exceed the ideal temperature of the ideal voltage. Even if the specific environment is a low-temperature environment, the membrane temperature can be maintained at the ideal temperature by controlling the detection voltage. Thus, the effect of the environmental factors can be reduced, and the sensitivity and identification ability of the sensor 10 is accurate and stable.

Figure 3A:
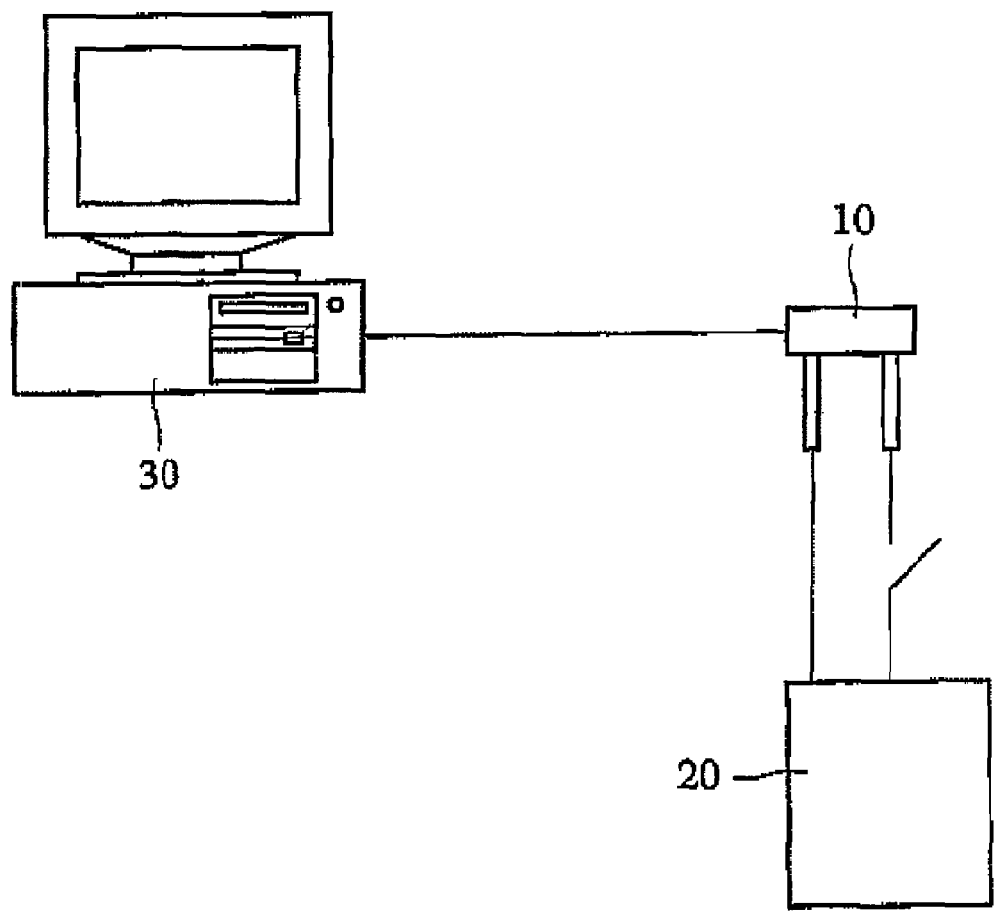
FIG. 3A is a schematic view showing an embodiment of the conventional intelligent gas identification system.
Figure 3B:
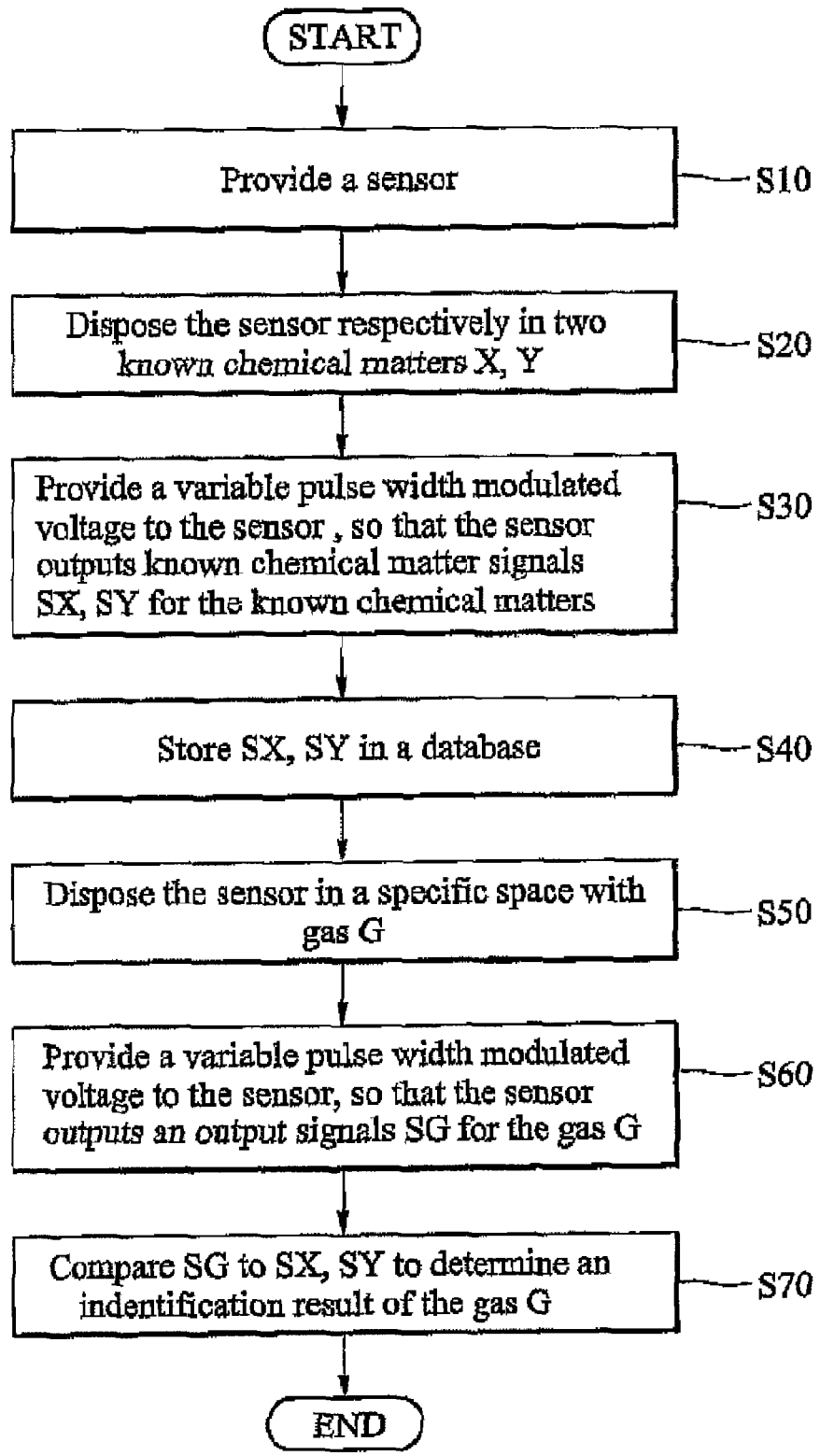
FIG. 3B is a flowchart showing the conventional method of gas identification.
Figure 7:
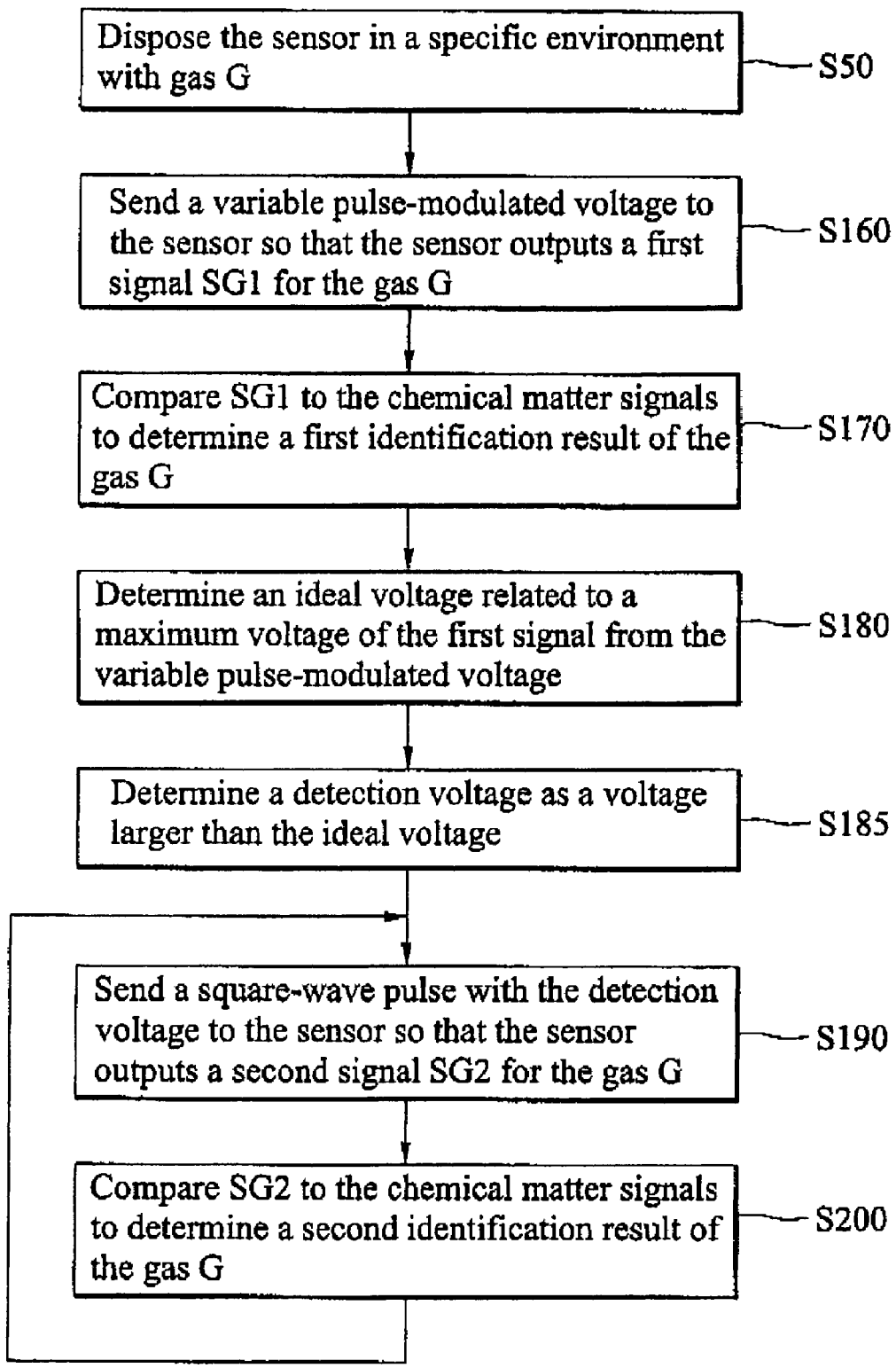
FIG. 7 is a flowchart showing the method of pulse-type gas concentration measurement of the present invention.

A further embodiment of the method of pulse-type gas concentration measurement of the present invention can be described with reference to the flowchart of FIG. 7. The embodiment assumes that a gas G exists in a specific environment to be identified. When the gas is to be identified, a plurality of chemical matter characteristics signals are obtained according to steps S10 to S40 in FIG. 3B.

The sensor 10 is then disposed in the specific environment with the gas G (step S50). The sensor 10 is provided with a variable pulse, such as a variable pulse-modulated voltage, so that the sensor outputs a first signal SG1 corresponding to the gas G in the specific environment (step S160). Thus, the processing device 30 receives the first signal SG1 and compares the first signal SG1 to the chemical matter characteristics signals to determine a first identification result for the gas G (step S170). When the gas G is a pure substance, the first identification result can be concentration of the gas; when the gas G is a mixture, the first identification result includes composition of the gas and concentration of the respective constituents of the gas.

The processing device 30 then determines a detection voltage according to the first signal SG1. Specifically, the processing device 30 determines an ideal voltage related to a maximum voltage of the first signal SG1 from the variable pulse-modulated voltage (step S180), and determines the detection voltage as a voltage larger than the ideal voltage (step S185).

The pulse power supply module 20 then sends a square-wave pulse with the detection voltage (e.g. the square-wave pulse of 5V in FIG. 6A) to the sensor 10 through the voltage input element, so that the sensor 10 outputs a second signal SG2 (e.g. the pulse in FIG. 6B) for the gas G to the processing device 30 through the output element (step S190). Thus, the processing device 30 compares the second signal SG2 to the chemical matter characteristics signal to determine a second identification result of the gas G (step S200), such as the concentration of respective constituents of the gas.

It should be mentioned that in order to perform the process of sending a variable pulse-modulated voltage to the sensor 10 to obtain the first signal, each pulse of the pulse-modulated voltage can be maintained for a specific period, such as three to five seconds, to ensure the membrane temperature of the sensing element reaches a steady temperature. However, a short period, such as one second or hundreds of milliseconds, is also acceptable.

Further, each pulse of the square-wave pulse can be maintained for a longer period of as three to five seconds or a shorter period of one second or hundreds of milliseconds according to environmental factors. However, an interval Td is required between each pulse of the square-wave pulse to reduce inaccuracy due to temperature variation of the sensing element of the sensor 10. Thus, the system and method of the present invention maintains accuracy and stability during operation.

With the present invention, a single sensor can be used to identify concentrations of at least two compositions of gases at the same time.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A pulse-type gas concentration measurement system, comprising:
    a sensor disposed in a specific environment, outputting a first signal and a second signal, wherein the sensor has a voltage input element, an output element and a sensing element;
    a pulse power supply module, connected to the voltage input element, sending a variable pulse-modulated voltage and a square-wave pulse with a detection voltage to the sensor through the voltage input element; and
    a processing device, connected to the output element of the sensor, storing a plurality of chemical matter characteristics signals, determining the detection voltage according to the first signal from the sensor and comparing the first signal with the chemical matter characteristics signals to determine composition of the gas and concentration of respective constituents of the gas, and comparing the second signal from the sensor to the chemical matter characteristics signal to determine the concentration of respective constituents of the gas.

2. The pulse-type gas concentration measurement system according to claim 1 wherein the processing device determines an ideal voltage related to a maximum voltage of the first signal from the variable pulse-modulated voltage, and determines the detection voltage as a voltage larger than the ideal voltage.

3. The pulse-type gas concentration measurement system according to claim 1, wherein the sensing element comprises a membrane of a metallic oxide.

4. The pulse-type gas concentration measurement system according to claim 3, wherein the metallic oxide comprises tin oxide ($SnO_2$).

5. A method of pulse-type gas concentration measurement, comprising the steps of:
    providing a sensor in a specific environment;
    sending a variable pulse to the sensor, so that the sensor outputs a first signal corresponding to gas in the specific environment;
    comparing the first signal with a plurality of chemical matter characteristics signals to determine a first identification result for the gas;
    determining a detection voltage according to the first signal;
    sending a square-wave pulse with the detection voltage to the sensor, so that the sensor outputs a second signal corresponding to the gas; and
    comparing the second signal with a plurality of chemical matter characteristics signals to determine a second identification result for the gas.

6. The method of pulse-type gas concentration measurement according to claim 5, wherein the first identification result and the second identification result for the gas respectively comprise the concentration of respective constituents of the gas.

7. The method of pulse-type gas concentration measurement according to claim 5, wherein the chemical matter characteristics signals are obtained by:
    disposing the sensor in a plurality of predetermined chemical matters and sending a variable pulse-modulated voltage to the sensor respectively, so that the sensor outputs each of the chemical matter characteristics signals corresponding to each of the predetermined chemicals; and
    storing the chemical matter characteristics signals in a database.

8. The method of pulse-type gas concentration measurement according to claim 5, wherein the variable pulse is a pulse-modulated voltage.

9. The method of pulse-type gas concentration measurement according to claim 5, wherein the first signal comprises a pulse voltage signal.

10. The method of pulse-type gas concentration measurement according to claim 9, wherein the step of determining the detection voltage according to the first signal further comprises:
    determining an ideal voltage related to a maximum voltage of the first signal from the variable pulse; and
    determining the detection voltage as a voltage larger than the ideal voltage.

11. A method of pulse-type gas concentration measurement, comprising the steps of:
    providing a sensor in a specific environment;
    sending a variable pulse to the sensor, so that the sensor outputs a first signal corresponding to a plurality of gases in the specific environment;
    comparing the first signal with a plurality of chemical matter characteristics signals to determine a first identification result for the gases;
    determining at least one detection voltage according to the first signal, wherein each detection voltage corresponds to one of the gases;
    sending at least one square-wave pulse with the detection voltage to the sensor, so that the sensor outputs at least one second signal corresponding to the gases; and
    comparing the second signal with a plurality of chemical matter characteristics signals to determine a second identification result for the gases.

12. The method of pulse-type gas concentration measurement according to claim 11, wherein the first identification result for the gases comprises composition of the gases.

13. The method of pulse-type gas concentration measurement according to claim 12, wherein the second identification result for the gases comprises concentration of respective constituents of the gases.

14. The method of pulse-type gas concentration measurement according to claim 11, wherein the chemical matter characteristics signals are obtained by:
  disposing the sensor in a plurality of predetermined chemical matter and sending a variable pulse-modulated voltage to the sensor respectively, so that the sensor outputs each of the chemical matter characteristics signals corresponding to each of the predetermined chemicals; and
  storing the chemical matter characteristics signals in a database.

15. The method of pulse-type gas concentration measurement according to claim 11, wherein the variable pulse is a pulse-modulated voltage.

16. The method of pulse-type gas concentration measurement according to claim 11, wherein the first signal comprises a pulse voltage signal.

17. The method of pulse-type gas concentration measurement according to claim 16, wherein the step of determining at least one detection voltage according to the first signal further comprises:
  determining at least one ideal voltage related to at least one maximum voltage of the first signal from the variable pulse; and
  determining each detection voltage as a voltage larger than each ideal voltage.

* * * * *